United States Patent [19]

Palumbo et al.

[11] Patent Number: 5,231,122
[45] Date of Patent: Jul. 27, 1993

[54] FIBROUS COMPOSITION FOR ABSORBENT PADS, A METHOD FOR THE MANUFACTURE OF AN ABSORBENT MATERIAL FROM SUCH A COMPOSITION, AND AN ABSORBENT MATERIAL PRODUCED BY THE METHOD

[75] Inventors: Gianfranco Palumbo, Pescara; Giovanni Carlucci, Chieti; Antonio D'Ambrosio, Pescara, all of Italy; Steffan Fors; Birgitta Johansson, both of Falun, Sweden

[73] Assignee: Faricerca S.p.A., Pescara, Italy

[21] Appl. No.: 798,062

[22] Filed: Nov. 27, 1991

Related U.S. Application Data

[63] Continuation of Ser. No. 335,410, Apr. 10, 1989, abandoned.

[30] Foreign Application Priority Data

Apr. 11, 1988 [IT] Italy .................. 67324 A/88

[51] Int. Cl.⁵ .................. C08L 97/02; C08L 9/00
[52] U.S. Cl. .................. 524/30; 524/13; 524/14; 524/543; 523/220; 428/220; 604/367; 604/370; 604/372; 604/374
[58] Field of Search .................. 524/13, 14, 30, 543; 604/367, 370, 374, 372; 523/220; 428/220

[56] References Cited

U.S. PATENT DOCUMENTS

| | | | |
|---|---|---|---|
| 4,216,772 | 8/1980 | Tsuchiya et al. | 604/372 |
| 4,364,992 | 12/1982 | Ito et al. | 428/398 |
| 4,458,042 | 7/1984 | Espy | 524/13 |
| 4,578,414 | 3/1986 | Sawyer et al. | 524/313 |
| 4,755,179 | 7/1988 | Shiba et al. | 604/370 |

FOREIGN PATENT DOCUMENTS

| | | |
|---|---|---|
| 0070164 | 1/1983 | European Pat. Off. . |
| 0099428 | 1/1984 | European Pat. Off. . |
| 0244486 | 11/1987 | European Pat. Off. . |
| 8403833 | 10/1984 | PCT Int'l Appl. . |

*Primary Examiner*—John Kight, III
*Assistant Examiner*—P. Hampton-Hightower
*Attorney, Agent, or Firm*—Sughrue, Mion, Zinn, Macpeak & Seas

[57] ABSTRACT

A fibrous composition for absorbent pads which, in addition to cellulose fibers, also contains first and second synthetic polymeric materials. At least the second polymeric material is constituted by synthetic fibers which have a higher melting point than that of the first polymeric material. The fibrous mixture is formed into the desired shape, for example, an absorbent body for disposable sanitary products, by pneumatic means. The absorbent body thus formed is then heat-treated to a temperature higher than the melting point of the first polymeric material but lower than that of the second polymeric material for a period of time so as to melt the first polymeric material and form bonding points or bridges between at least the synthetic fibers which have not melted and which constitute the second polymeric material. The absorbent body is cooled to a temperature such that the first polymeric material sets, bonding at least the synthetic fibers together so as to form a framework containing the cellulose fibers.

23 Claims, 3 Drawing Sheets

FIBROUS COMPOSITION FOR ABSORBENT PADS, A METHOD FOR THE MANUFACTURE OF AN ABSORBENT MATERIAL FROM SUCH A COMPOSITION, AND AN ABSORBENT MATERIAL PRODUCED BY THE METHOD

This is a continuation of application Ser. No. 07/335,410 filed Apr. 10, 1989, now abandoned.

FIELD OF THE INVENTION

The invention relates to a fibrous composition for absorbent pads, which is made of cellulose fibers and synthetic fibers. The invention also relates to a method for the manufacture of an absorbent material from the composition and to the absorbent article produced by the method.

DESCRIPTION OF THE PRIOR ART

Disposable sanitary articles, such as, for example, babies' nappies or sanitary towels for women, conventionally have absorbent cores constituted by pads of cellulose fibers produced by the deposition on a porous medium (form) from a flow of cellulose fibers and air. The cellulose fibers are produced by the dry grinding of a sheet of wood pulp, generally conifer wood pulp. This material is cheap and has a good capacity for absorbing body fluids.

In the case of absorbent pads formed with ground wood pulp, it is thought that the liquids are absorbed and retained mainly within the empty spaces which are formed in the network of cellulose fibers, rather than absorbed into individual fibers. The quantity of liquid absorbed by an absorbent body of cellulose fibers is therefore greater the lower its density, that is, the greater its bulk. Consequently, anything which affects the density and can cause the absorbent material to collapse will contribute to a reduction of its absorption capacity. An absorbent pad which is made of 100% cellulose fibers has low resistance to compression, particularly when wet, that is, the material is compressed considerably when it is subjected to pressure, and the pad does not therefore have a good capacity for retaining liquids under pressure, and thus has a low absorption capacity in use.

The absorption capacity of the absorbent pad can be increased by the addition of water-gelling substances which are generally defined as superabsorbent substances. On the other hand, the introduction of the superabsorbent substances does not completely resolve the problem since the absorbent pad still has little mechanical strength and often breaks in use, preventing the transfer of the liquids to parts which are still dry.

It is known that the strength of an absorbent layer can be increased by its being mixed with certain synthetic fibers. By way of example, the addition of polyolefin fibers to cellulose fibers in order to improve the degree of strength of the absorbent pad, once it has been heat-treated to activate the polyolefin fibers, is known from U.S. Pat. No. 4,458,042.

It is thought that bonding points develop between the cellulose fibers at the moment when the polyolefin fibers melt: the strength of the pad is thus increased.

The polyolefin fibers are very short (they have an average length of approximately 1 mm). This fact presumably increases the chance of the polyolefin fibers acting as a bonding agent between individual cellulose fibers, but the polyolefin fibers completely lose their fibrous characteristics once they are melted. In the finished product, they therefore act as a glue which binds the cellulose fibers together.

An absorbent pad prepared in this manner will have greater strength and a good capacity for absorbing liquids, but a fairly low retention capacity.

In fact, when an absorbent pad soaked with liquid is subjected to pressure, the wet cellulose fibers lose their resilience and the whole pad collapses, regardless of the fact that the cellulose fibers are interconnected to form a framework.

The whole absorbent layer will therefore collapse if subjected to pressure when wet and the liquid will be expelled from the absorbent layer, regardless of the fact that the fibers are bonded together.

It is also known to improve the wettability of synthetic fibers or mixtures of cellulose and synthetic fibers by the treatment of the synthetic fibers with surfactants which develop hydrophilic characteristics in the synthetic fibers.

According to the above-mentioned U.S. Pat. No. 4,458,042, a surfactant selected from a group constituted by non-ionic and ionic surfactants with molecular weights of less than approximately 8000 is used.

The U.S. Pat. No. 4,578,414 proposes, as a surfactant for polyolefin fibers, any one of the following group of materials comprising:

a) an alkylphenol alkoxylate together with or in combination with a mixture of a mono-, a di-, and/or a tri-glyceride, or
b) a polyoxyalkylene ester of a fatty acid, or
c) a combination of b) and any compound from a).

For more detailed information concerning these agents, which can make polyolefin fibers hydrophilic, reference is made to the contents of the above-mentioned U.S. patent specification.

THE OBJECT OF THE INVENTION

The object of the invention is to propose a fibrous composition containing synthetic fibers and cellulose fibers, for the production of an absorbent material, which after heat treatment has good strength of shape even in wet conditions and under pressure.

By means of this invention, an absorbent material is produced which not only has increased strength of shape, but also an increased capacity for retaining the liquid absorbed (absorption capacity).

SUMMARY OF THE INVENTION

According to the invention, in addition to cellulose fibers, the composition contains a first and a second synthetic polymeric material.

At least the second polymeric material is constituted by synthetic fibers. Moreover, the melting point of the first polymeric material is lower than that of the second polymeric material.

At least the second polymeric material is constituted by quite long fibers, which means that at least 90% by weight of the fibers have lengths between 3 and 60 mm, and conveniently lengths between 5 and 20 mm.

The first polymeric material, which has the lower melting point, may be constituted by very short fibers, for example, of an average length of approximately 1 mm, in accordance with U.S. Pat. No. 4,458,042, in order to improve the chance of this fiber fraction to act as a bonding agent in the finished product, or may be constituted by polymeric materials in powder form.

Preferably, all the synthetic fibers are constituted by two-component fibers, in which a first component is constituted by the first polymeric material and the second component consists of the second polymeric material.

In this case, the two-component fibers are longer which means that at least 90% by weight of the two-component fibers have lengths between 3 and 60 mm and preferably lengths between 5 and 20 mm.

In this case, the fineness of the fibers may be between 1 and 10 dtex, preferably between 1.5 and 7 dtex and even more preferably between 1.7 and 4.4 dtex (1 dtex=0.9 denier).

The two components of the two-component fibers may be arranged side by side or, alternatively, one of the components, consisting of the first polymeric material, may cover the second component which consists of the second polymeric material. In any case, the second component has a higher melting point than the first component. The second polymeric material conveniently has a melting point at least 15 C. degrees higher than the first polymeric material.

The two-component fibers are preferably curled and if there are fibers and/or powder of the first polymeric material and fibers of the second polymeric material, then the latter are preferably curled.

The fibrous composition conveniently contains a percentage of from 2% to 80% by weight of synthetic fibers, calculated on the total weight of the fibrous composition. Even more preferably, the percentage of synthetic fibers is from 10% to 40% of the total weight of the fibrous mixture.

The first polymeric material may be constituted by any thermoplastic material which has a melting point at least 15 C. degrees lower than that of the second polymeric material, which may be constituted by polyethylene, polypropylene, copolymers of esters or of esters and other monomers, or copolymers of amides or of amides and other monomers.

One or both of the thermoplastic polymeric materials may be treated according to known principles, with one or more surfactants (that is, agents which make the surfaces of the synthetic fibers substantially more hydrophilic), or one or more surfactants may be incorporated in one or in both the thermoplastic polymeric materials.

For example, the surfactants of the type described by U.S. Pat. No. 4,578,414 have been shown to be suitable. The synthetic fibers and the cellulose fibers may be wet mixed during the normal manufacture of the sheets of cellulose produced from wood pulp and, in this case, the presence of the surfactants may also facilitate the intimate mixing of the synthetic fibers and the cellulose fibers which go to form the densified sheet of synthetic fibers and cellulose fibers in a wholly conventional manner similar to the normal manufacture of cellulose sheets from wood pulp. In this case, the sheet is then dry fiberized according to normal methods known to manufactures of absorbent products.

Alternatively, the cellulose fibers and the synthetic components may be dry mixed, the various fibers (cellulosic and synthetic) being the dry fiberized or reopened according to known techniques and mixed mechanically and/or pneumatically. The presence of the surfactant which impregnates or covers the synthetic fibers has the main function of making the fibers more hydrophilic and therefore more absorbent in the absorbent pad.

In any case, once the fibrous composition constituted by an intimate mixture of cellulose fibers and synthetic fibers has been made, it is dry formed into the shape of the designated article (e.g. an absorbent body for a baby diaper, an absorbent body for a sanitary towel, etc.) by pneumatic means according to techniques known to the manufacturers of absorbent products.

It is, however, a characteristic of the invention that whatever the desired shape of the absorbent body of the absorbent article, it is then heated to a temperature higher than the melting point of the first polymer, but lower than the melting point of the second polymer, for a period of time sufficient for the first polymeric material to melt and form bonding points or bridges between at least the higher melting-point synthetic fibers.

Once the absorbent body has cooled, the first synthetic polymeric material sets to link together at least the fibers of the second polymeric material. The fibers of the second polymeric material form a framework of synthetic fibers containing the absorbent material.

This structure has excellent mechanical strength, even when wet, mechanical strength meaning tensile strength, compression strength and resilience.

The good tensile-strength characteristics prevent the absorbent body from breaking in use and therefore avoid the phenomenon of lack of capillary transfer of the liquids to parts of the absorbent body which are still unused.

The good compression strength characteristics mean that the structure yields less under the loads of use and therefore has an improved absorption capacity (the retention of liquids under load).

Finally, the good resilience characteristics, resilience meaning the capacity to regain as much of the undeformed shape as possible after a deforming load has been removed, and therefore to absorb a further quantity of liquid after deformation, means that the absorbent body proposed by the present invention is a definite improvement relative to those of the prior art. Whilst it is not wished to be bound by particular theories, it would appear that the improvement in absorptive capacity and resilience is due to the presence of the framework of synthetic fibers which are very resilient both when dry and when wet, unlike the heat-bonded absorbent structures of the prior art, such as that described by U.S. Pat. No. 4,458,042. The bonded fibers seem to constitute a kind of load-bearing structure containing the absorbent cellulose fibers. On the other hand, the structure according to the above-mentioned patent is formed by the same cellulose fibers held together by the fused synthetic material. However, the cellulose fibers are reasonably strong and resilient only when dry and the pseudo-structure therefore collapses under the loads of use, regardless, or almost regardless, of the fact that the cellulose fibers are bonded together.

DETAILED DESCRIPTION OF THE DRAWINGS

The invention will now be described, purely by way of non-limiting example, with reference to the appended drawings, in which.

Figure 1:
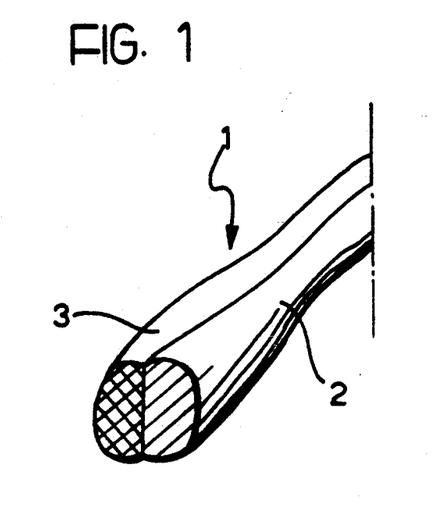
FIG. 1: shows schematically a first type of two-component fiber.

With reference first to FIG. 1, a two-component fiber is generally indicated 1. In accordance with the invention, it is constituted by two components. A first component 2 consists of a first polymeric material, and a second component 3 consists of a second polymeric material. The two components 2 and 3 in this case are arranged side by side.

In this embodiment, the first material 2 consists of polyethylene whilst the second polymeric material 3 consists of polypropylene.

The two components 2 and 3 are thus polyolefins.

The melting point of the PE component is approximately 130° C. whilst the pp component has a melting point of approximately 165° C. The ratio of the PE/PP fractions in the two-component fiber is approximately 50/50.

Figure 2:
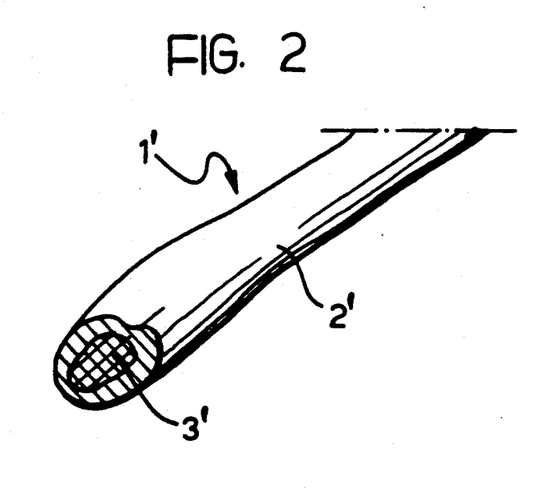
FIG. 2: shows schematically a second type of two-component fiber.

FIG. 2 shows an alternative two-component fiber 1'. The outer layer 2' in this case consists of PE of the same type as that used in the previous embodiment whilst the inner material 3' consists of pp, also of the same type as that used in the previous embodiment.

In the tests carried out, the two-component fibers 1 of the PE/PP type were mixed with cellulose fibers of the Stora Fluff type (the trade name of Stora Kopparbergs Bergslag AB).

In one case, the two-component fibers 1 were substantially straight fibers and, in this case, the first polymeric material, polyethylene, contained a first surfactant of the type described in U.S. Pat. No. 4,578,414. Moreover, the fiber was treated with a second surfactant of conventional type, belonging to the sulphosuccinate family.

In another case, a mixture was studied which contained two-component fibers 1 with the same polymeric structure, but in which the fibers had been treated solely with the second type of conventional surfactant. These fibers were curled.

The finenesses of the two-component fibers tested in the compositions given in the tables were in the range 2.2 to 3.3 dtex.

The ratio by weight of the two-component fibers to the cellulose fibers in the mixture was 30/70 in both cases.

In the tests described in Table 1, the two-component fibers were mixed with the cellulose fibers in wet conditions before the drying section of a machine for the continuous production of cellulose pulp from wood. A moist web of fibrous mixture was formed from the mixed paste and was then dried and cut into sheets.

Still with reference to the examples given in Table 1 and Table 2, the cellulose fibers were also mixed with another type of synthetic fiber, known under the trade name HERCULES E338 PULPEX, produced by Hercules Inc., U.S.A. This is constituted by a single-component polyolefin fiber, more precisely, a polyethylene fiber treated in accordance with U.S. Pat. No. 4,458,042. These fibers were mixed in the same ratio of 30/70 by weight as the two-component fiber 1, and the fibrous composition was formed in the same manner.

Sheets consisting of 100% Stora Fluff were also produced as a reference material.

After dry-fiberizing of the various sheets in a hammer mill, samples were formed from the various fibrous compositions indicated in Table 1 and were tested for their absorption times and their absorptive capacities according to the Scan C 33:80 standard (issued by the Scandinavian Pulp, Paper and Board Testing Committee, Stockholm, Sweden), and for the strength of the pad according to the PFI 1981 method (method for determining the strength of a fibrous pad established by the Norwegian PAPIRINDUSTRIENS FORKNINGSINSTITUTT). All the samples were heat-treated in an oven at the temperatures indicated in Table 2.

The results of the tests described are given in Tables 1 and 2 below.

TABLE 1

CHARACTERISTICS OF THE SHEETS OF FIBROUS COMPOSITION PRODUCED WET

|  | Composition 1 | Composition 2 | Composition 3 | Composition 4 |
| --- | --- | --- | --- | --- |
| Weight in grams g/m$^2$ | 865 | 866 | 878 | 942 |
| Thickness mm | 2.97 | 3.13 | 2.58 | 1.68 |
| Density Kg/m$^3$ | 291 | 277 | 340 | 561 |
| Percentage by weight of synthetic fibers % | 30 | 30 | 30 | — |
| Percentage by weight of cellulose fibers % | 70 | 70 | 70 | 100 |

Note:
Composition 1: the synthetic fibers are curled, two-component fibers of the type indicated in FIG. 1 and have a PE/PP composition in a proportion of 50/50. They are produced by JACOB HOLM VARDE, Denmark, under the name DANAKLON ES. The fiber is treated with surfactants.
Composition 2: the synthetic fibers are similar two-component fibers but are modified with respect to those of composition 1. In particular, they are straight instead of curled and the PE of the two-component fiber is treated with a surfactant of the type described by U.S. Pat. No. 4578414. The fiber is also treated with surfactants in this case.
Composition 3: the synthetic fibers are constituted by Pulpex E 338 polyethylene fibers from the American company Hercules Inc.
In all cases, the cellulose fibers were STORA FLUFF fibers of STORA KOPPARBERGS BERGSLAG AB, Sweden.

TABLE 2

ABSORPTION CHARACTERISTICS OF THE SAMPLES ACCORDING TO THE COMPOSITIONS OF TAB. 1 PRODUCED ACCORDING TO THE SCAN C 33:80 STANDARD, HEAT-TREATED AND SUBJECTED TO A PRESSURE OF 7.5 KPa, AND STRENGTH CHARACTERISTICS ACCORDING TO PFI 1981

|  | Composition 1 | | Composition 2 | | Composition 3 | Composition 4 |
| --- | --- | --- | --- | --- | --- | --- |
| Heat-treatment temperature °C. | 135 | 145 | 135 | 145 | 145 | 145 |
| Specific volume when dry dm$^3$/Kg | 14.4 | 16.3 | 13.5 | 14.3 | 11.2 | 13.1 |
| Absorption capacity g/g | 7.7 | 7.8 | 6.7 | 7.1 | 5.9 | 6.4 |
| Absorption time s | 5.4 | 7.2 | 3.1 | 3.4 | 6.4 | 3.2 |
| Strength N | >15* | >15* | >15* | >15* | >15* | 6.4 |

*The strength-measuring equipment only determines values below 15N.

Table 1 indicates the characteristics of the sheets of the various fibrous compositions tested.

From the values derived from Table No. 2, it can be seen that the samples formed from the compositions No. 1 and No. 2 according to the present invention have strengths at least equal to those of samples No. 3 formed from cellulose fibers heat-bonded to the Pulpex E338 synthetic fibers but have much greater absorption capacities. Moreover, the samples No. 1 and No. 2 containing two-component fibers also show an improvement in absorption capacity compared with samples No. 4 which are made solely from cellulose fibers, whilst sample No. 3 has a lower absorption capacity than sample No. 4 which is constituted solely by non-heat-bonded cellulose fibers.

Samples No. 1 and No. 2 also show good results as regards their absorption times. In particular, sample No. 2 has absorption times which are entirely comparable with those of sample No. 4, but has a greater absorption capacity.

The characteristics of resilience of the pads produced in accordance with the present invention are shown in Table 3 below and in FIG. 4.

TABLE 3

| RESILIENCE CHARACTERISTICS | Composition 1 | Composition 2 | Composition 3 | Composition 4 |
|---|---|---|---|---|
| $V_2$: Wet bulk at 20 KPa dm$^3$/Kg | 6.1 | 5.8 | 4.7 | 4.8 |
| $V_1$: Wet bulk after removal of load dm$^3$/Kg | 12.5 | 12.2 | 8.0 | 8.9 |
| $RI = \dfrac{V_1 - V_2}{V_2}$ = resilience index % | 105 | 110 | 71 | 85 |

The compositions of the samples indicated in Table 3 are the same as those indicated in Table 1, with the difference that the samples are of a different shape and were produced from fibrous compositions obtained by the dry mixing of the individual components of the compositions indicated in Table 1, in the same proportions. Naturally, this falls completely within the spirit and scope of the present invention, which is not limited to the wet mixing of the different individual fibers to produce a sheet of fibrous composition as described above with reference to the samples of Tables No. 1 and No. 2. In fact, it may also be operatively convenient for a producer of absorbent products to start with a normal sheet of cellulose pulp, which is dry-fiberized according to known techniques, and with synthetic fibers (for example in bales) opened up according to known techniques, the synthetic fibers and the cellulose fibers then being dry mixed mechanically and/or pneumatically to produce the fibrous compositions according to the present invention.

The samples of Table No. 3 are constituted by samples with square bases with sides of 38 mm. The sample is dry formed in a square-based sample former operating under vacuum according to known principles similar to those described by the SCAN C:80 standard already mentioned, starting with a dry mixture of cellulose fibers and synthetic fibers intimately mixed beforehand in the ratios indicated in Table 1.

The weight of each individual sample was 2.21 g. Once formed, the samples were subjected to heat-treatment, being heated to temperatures of approximately 135° C. The samples were then allowed to cool to ambient temperature, and then removed from the square formers. In the example given in Table 3, 100% of the sample No. 4 was constituted by cellulose fibers produced by the dry-fiberizing of a sheet of STORA FLUFF pulp such as that of Table 2, with the difference that in this case the sample was not heat-treated.

Once the square-based samples had been formed as described above, they were completely soaked and then subjected to a cycle of compressions with a dynamometer in the loading range which corresponds to pressures of from 5 to 20 KPa. The dynamometer continuously monitored the depths of the samples and the compression load applied. The speed at which the samples were compressed was 10 mm/1'. FIG. 4 gives the bulks which correspond to the various loads. Table 3, however, shows the bulks at 20 KPa and the bulks regained by the samples after the removal of the load.

The high bulk values of the samples constituted by the fibrous compositions 1 and 2 according to the present invention can be seen from Table 3. These values are undoubtedly higher than those of the sample No. 4 which is made only of cellulose fibers, whilst the sample No. 3 again has lower absolute values than the sample No. 4 taken as a reference.

If a resilience index RI is defined as:

$$RI = \frac{V_1 - V_2}{V_2} \times 100$$

the data of Table 3 show that the reference sample 4 has an $(RI)_4 = 85\%$, the sample 3 has an $(RI)_3 = 71\%$, whilst the compositions 1 and 2 according to the present invention have RIs > 100%, in particular $(RI)_1 = 105\%$ and $(RI)_2 = 110\%$.

This greater resilience of the fibrous compositions according to the present invention, that is, their greater capacity to regain their undeformed volume once the deforming load has been removed, is a very important characteristic, particularly in consideration of the use for which the heat-stabilised pads according to the present invention are intended. In fact, a disposable sanitary product, such as, for example, a sanitary towel or a baby's nappy, is subject in use to considerable forces which can make a structure made only of cellulose fibers collapse, even if it is heat-bonded. However, an absorbent pad made according to the present invention can resist considerable compressione, whilst retaining a greater quantity of fluid within it (as shown in Table 2 above) and, in particular, can absorb a further quantity of liquid once the load has been removed since it tends to regain its undeformed shape.

It will be appreciated that this particular characteristic of the present invention can prevent the premature loss of the functioning of the structures for absorbing body fluids. For example, in a sanitary towel, this greater resilience means that the absorbent body of the present invention adapts itself better to the anatomy and, moreover, is better at conforming dynamically to anatomical shapes and following the different geometries which occur during the use of a sanitary towel.

Therefore, according to the invention, a heat-bonded structure of cellulose fibers and synthetic fibers is obtained which can appreciably resist compression forces under wet conditions and thus provide improved liquid retention. Moreover, the structure is notably resilient when damp, that is, as described, and, unlike structures which are not heat-bonded, or which are heat-bonded according to the prior art (sample No. 3, Table 3), it can retain a considerable volume once a deforming load has been removed.

Figure 3:
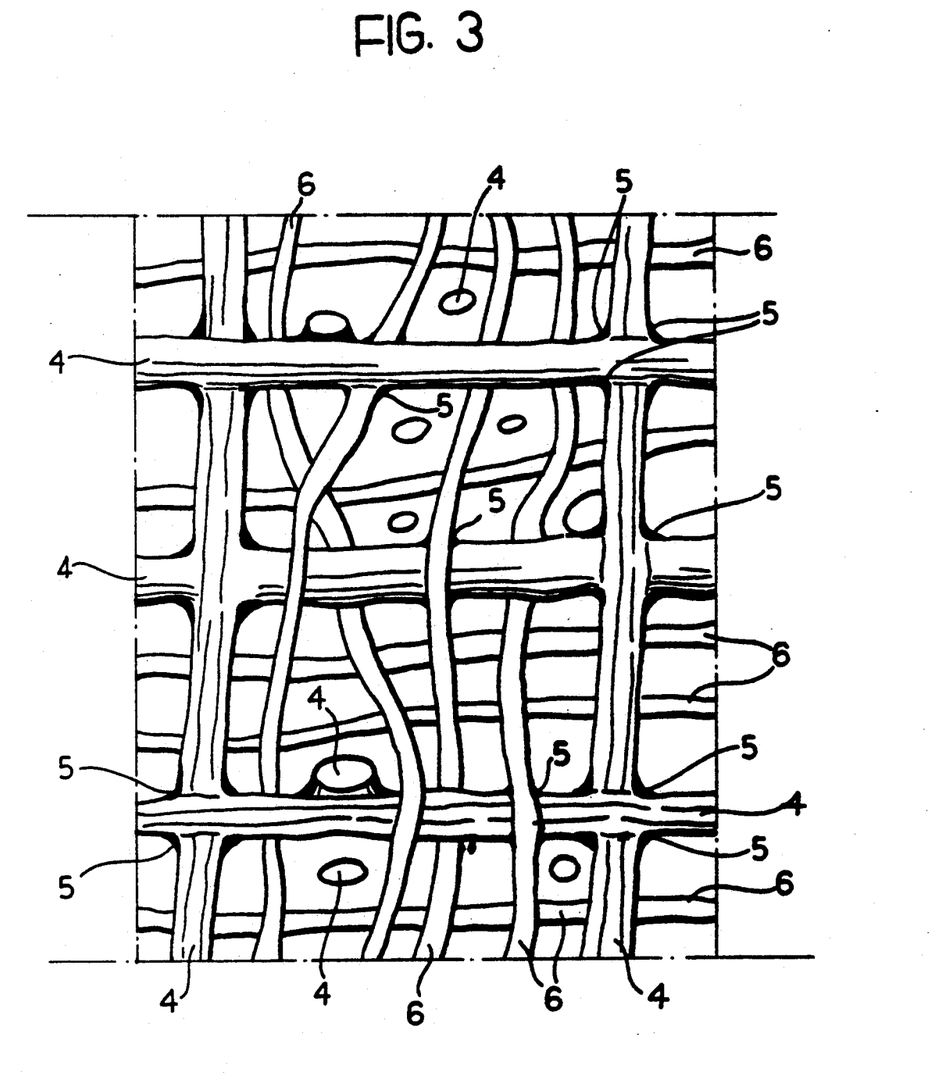
FIG. 3: shows schematically the structure of the absorbent material according to the invention.

Finally, FIG. 3 shows very schematically the structure of the absorbent material according to the present invention, after heat-treatment. In the drawing, the synthetic fibers are indicated 4. It will be noted that, at the points of contact of adjacent synthetic fibers, the synthetic fibers are joined together so that the low melting-point polymeric component forms bonding points between the fibers. That is, it acts as glue between the various fibers. It should also be noted that the low melting-point polymer 2 (shown in FIG. 1) is distributed substantially around the fibers which do not melt. Since the polymer 2 contains materials which make it wettable, the whole synthetic fiber thus develops hydrophilic characteristics.

The cellulose fibers are indicated 6 in FIG. 3. It will be noted that some of these fibers adhere to the synthetic fibers, although most are simply contained within the polymeric framework. With reference to the physical shape of the two-component fibers, the curled fibers develop a more bulky three-dimensional structure.

Figure 4:
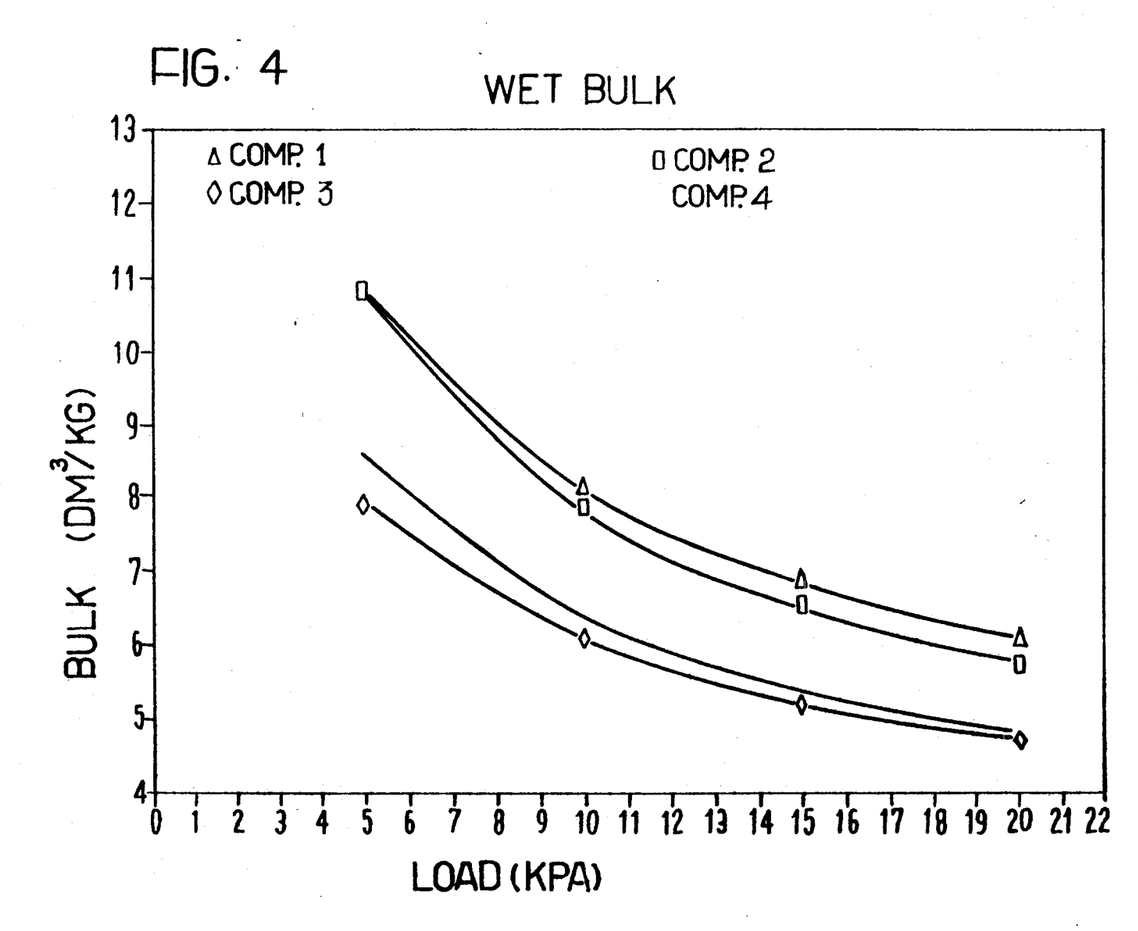
FIG. 4: is a graph showing a comparison between the wet bulks of absorbent materials in accordance with the present invention and prior-art absorbent materials under different loads.

The graph of FIG. 4 shows the wet bulk of the samples (already described with reference to Table No. 3) when subjected to increasing loads corresponding to pressures of from 5 KPa to 20 KPa. It is noted that the samples of compositions 1 and 2 according to the present invention show decidedly greater wet bulk values than the compositions 3 and 4 throughout the range of loads. On average, the wet bulk of the samples 1 and 2 is more than 20% greater throughout the range of loads. Naturally, the wet bulks of the various samples at 20 KPa are the same as given in Table No. 3.

Therefore, according to the present invention, an absorbent fibrous composition is obtained which, once transformed into an absorbent body for disposable sanitary products, not only has better characteristics of shape, but also a better absorptive capacity in use and better resilience characteristics. It therefore enables absorbent bodies to be produced which are lighter in weight and therefore generally thinner for a given absorptive capacity than those of the prior art, or which, for a given overall weight, enable absorbent bodies of greater absorptive capacity to be produced. In any case, the absorbent bodies produced in accordance with the present invention have better resilience charateristics and are better at adapting to and dynamically following the anatomical shapes of the user.

Naturally, the present invention is not limited to two-component fibers of PE and PP as described, on the contrary, different combinations of polymeric materials are possible, as shown by way of example in Table 4 below.

TABLE 4

| First polymer | | Second polymer | |
|---|---|---|---|
| Type | Melting point °C. | Type | Melting point °C. |
| PE | 130 | PP | 165 |
| PE | 130 | PET | 265 |
| PP | 165 | PET | 265 |
| PE | 130 | PA 6 | 210 |
| PE | 130 | PA 6.6 | 250 |
| PP | 165 | PA 6 | 210 |
| PP | 165 | PA 6.6 | 250 |
| PA 6 | 210 | PET | 265 |
| PA 6.6 | 250 | PET | 265 |
| CoPA | 130–200 | PET | 265 |
| CoPA | 130–200 | PA 6 | 210 |
| CoPA | 130–200 | PA 6.6 | 250 |
| CoPET | 130–210 | PET | 265 |

TABLE 4-continued

| First polymer | | Second polymer | |
|---|---|---|---|
| Type | Melting point °C. | Type | Melting point °C. |
| CoPET | 130–210 | PA 6.6 | 250 |

Note:
PA = Polyamide
PET = Polyester
PP = Polypropylene
PE = Polyethylene

We claim:

1. An absorbent fibrous composition comprising a mixture of cellulose fibers and at least first and second polymeric materials wherein the first and second polymeric materials are present as a two component synthetic fiber, wherein the at least first and second polymeric materials are arranged side by side in said two component synthetic fiber or wherein the first polymeric material is arranged around the second polymeric material, said first and second polymeric materials comprising from 2 to 80% by weight of the fibrous composition wherein at least one of said first and second polymeric materials comprises a surfactant which renders the polymeric material permanently hydrophilic, wherein the first polymeric material has a melting point at least 15° C. lower than that of the second polymeric material, wherein said absorbent fibrous composition is heated to a temperature at least equal to the melting point of the first polymeric material but lower than the melting point of the second polymeric material for a period of time sufficient for the first polymeric material to melt and form bonding points between the two component synthetic fibers present and yield a polymeric framework which is a load-bearing structure which contains the majority of said cellulose fibers contained within said polymeric framework but not bonded to said at least first and second polymeric materials, which absorbent fibrous composition exhibits good shape retention under wet conditions and under pressure, wherein said at least first and second polymeric materials are selected from combinations from the group consisting of polyethylene and polypropylene; polyethylene and polyester; polypropylene and polyester; polyethylene and polyamide; and polyamide and polyester.

2. A fibrous composition according to claim 1, wherein at least 90% by weight of the synthetic fibers of the second polymeric material have lengths of between 3 and 60 mm.

3. A fibrous composition according to claim 2, wherein at least 90% by weight of the synthetic fibers of the second polymeric material have lengths of between 5 and 20 mm.

4. A fibrous composition according to claim 1, wherein the synthetic fibers of the second polymeric material have a fineness of between 1 and 10 dtex.

5. A fibrous composition according to claim 4, wherein the synthetic fibers have a fineness of between 1.5 and 7 dtex.

6. A fibrous composition according to claim 1, containing fibers of the first polymeric material and fibers of the second polymeric material.

7. A fibrous composition according to claim 1, wherein the two-component fibers and at least the fibers of the second polymeric material respectively, are curled.

8. A fibrous composition according to claim 1, wherein the surfactant consists of at least one of the following agents:
   a) an alkylphenol alkoxylate together with or in combination with a mixture of a mono-, a di-, and/or a tri-glyceride,
   b) a polyoxyalkylene ester of a fatty acid,
   c) a combination of b) and any compound from a).

9. A fibrous composition according to claim 1, wherein the first polymeric material consists of fibers having lengths no longer than 1 mm.

10. A fibrous composition according to claim 1, wherein the first synthetic polymeric material consists of a powder and fibers having lengths no longer than 1 mm.

11. A fibrous composition according to claim 1, produced by the wet mixing of the cellulose fibers and the polymeric materials, which composition is in dried-sheet form.

12. A fibrous composition according to claim 1, produced by the dry mixing of the cellulose fibers and the polymeric materials.

13. An absorbent body according to claim 1, wherein at least some of the cellulose fibers contained in the framework are bonded to the framework by means of the first polymeric material.

14. The method of claim 1, wherein the cellulose fibers are derived from a material selected from the group consisting of chemical wood pulp, chemically modified thermomechanical wood pulp, thermomechanical wood pulp, mechanical wood pulp, and mixtures thereof.

15. A disposable absorbent article according to claim 1, wherein the cellulose fibers are derived from a material selected from the group consisting of chemical wood pulp, chemically modified thermomechanical wood pulp, thermomechanical wood pulp, mechanical wood pulp, and mixtures thereof.

16. A fibrous composition according to claim 1, wherein said first and second polymeric materials comprise from 10 to 40% by weight of the fibrous composition.

17. A method for the production of an absorbent body for disposable sanitary products comprising a mixture of cellulose fibers and at least first and second polymeric materials wherein the first and second polymeric materials are present as a two component synthetic fiber, wherein the at least first and second polymeric materials are arranged side by side by side in said two component synthetic fiber or wherein the first polymeric material is arranged around the second polymeric material, said first and second polymeric materials comprising from 2 to 80% by weight of the absorbent body, wherein at least one of said first and second polymeric materials comprises a surfactant which renders the polymeric material permanently hydrophilic, wherein the first polymeric material has a melting point at least 15° C. lower than that of the second polymeric material, which absorbent body exhibits good shape retention under wet conditions and under pressure, wherein said at least first and second polymeric materials are selected from combinations from the group consisting of polyethylene and polypropylene; polyethylene and polyester; polypropylene and polyester; polyethylene and polyamide; and polyamide and polyester, which method comprises the steps of:

forming the mixture of cellulose fibers and the at least first and second polymeric materials into the absorbent body of a desired shape;

heating the absorbent body to a temperature at least equal to the melting point of the first polymeric material but below the melting point of the second polymeric material for a period of time sufficient for the first polymeric material to melt and form bonding points between the two component synthetic fibers present and yield a polymeric framework which is a load-bearing structure which contains the majority of said cellulose fibers contained within said polymeric framework but not bonded to said at least first and second polymeric materials; and cooling the absorbent body to a temperature such that the first polymeric material resolidifies and at least the synthetic fibers are bonded together to form a framework comprising the synthetic fibers containing the cellulose fibers.

18. The method of claim 17, wherein said first and second polymeric materials comprise from 10 to 40% by weight of the fibrous composition.

19. A disposable absorbent article comprising a mixture of cellulose fibers and at least first and second polymeric materials wherein the first and second polymeric materials are present as a two component synthetic fiber, wherein the at least first and second polymeric materials are arranged side by side in said two component synthetic fiber or wherein the first polymeric material is arranged around the second polymeric material, said first and second polymeric materials comprising from 2 to 80% by weight of the disposable absorbent article, wherein at least one of said first and second polymeric materials comprises a surfactant which renders the polymeric material permanently hydrophilic, wherein the first polymeric material has a melting point at least 15° C. lower than that of the second polymeric material, wherein said disposable absorbent article is heated to a temperature at least equal to the melting point of the first polymeric material but lower than the melting point of the second polymeric material for a period of time sufficient for the first polymeric material to melt and form bonding points between the two component synthetic fibers present and yield a polymeric framework which is a load-bearing structure which contains the majority of said cellulose fibers contained within said polymeric framework but not bonded to said at least first and second polyeric materials, which disposable absorbent article exhibits good shape retention under wet conditions and under pressure, wherein said at least first and second polymeric materials are selected from combinations from the group consisting of polyethylene and polypropylene; polyethylene and polyester; polypropylene and polyester; polyethylene and polyamide; and polyamide and polyester.

20. The disposable absorbent article of claim 19, wherein the first and second polymeric materials comprise from 10 to 40% by weight of the disposable absorbent article.

21. A disposable sanitary product comprising a mixture of cellulose fibers and at least first and second polymeric materials wherein the first and second polymeric materials are present as a two component synthetic fiber, wherein the at least first and second polymeric materials are arranged side by side in said two component synthetic fiber or wherein the first polymeric material is arranged around the second polymeric material, said first and second polymeric materials comprising from 2 to 80% by weight of the disposable sanitary product, wherein at least one of said first and second polymeric materials comprises a surfactant which renders the polymeric material permanently hydrophilic, wherein the first polymeric material has a melting point at least 15° C. lower than that of the second polymeric material, wherein said disposable sanitary product is heated to a temperature at least equal to the melting point of the first polymeric material but lower than the melting point of the second polymeric material for a period of time sufficient for the first polymeric material to melt and form bonding points between the two component synthetic fibers present and yield a polymeric framework which is a load-bearing structure which contains the majority of said cellulose fibers contained within said polymeric framework but not bonded to said at least first and second polymeric materials, which disposable sanitary product exhibits good shape retention under wet conditions and under pressure, wherein said at least first and second polymeric materials are selected from combinations from the group consisting of polyethylene and polypropylene; polyethylene and polyester; polypropylene and polyester; polyethylene and polyamide; and polyamide and polyester.

22. The disposable sanitary product of claim 21, wherein said first and second polymeric materials comprise from 10 to 40% by weight of the disposable sanitary product.

23. A fibrous composition according to claim 4, wherein the synthetic fibers have a fineness of between 1.7 and 4.4 dtex.

* * * * *